US012638458B2

(12) United States Patent
Rannou et al.

(10) Patent No.: US 12,638,458 B2
(45) Date of Patent: May 26, 2026

(54) SERS METHOD FOR ANALYZING A VISCOUS BIOFLUID

(71) Applicants: ASSISTANCE PUBLIQUE-HOPITAUX DE PARIS, Paris (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR); UNIVERSITÉ DE REIMS CHAMPAGNE-ARDENNE, Reims (FR); UNIVERSITE PARIS CITE, Paris (FR)

(72) Inventors: François Rannou, Paris (FR); Amanda Robinson, Le Kremlin-Bicêtre (FR); Didier Borderie, Paris (FR); François Etienne, Rouen (FR); Cyril Gobinet, Athies-sous-Laon (FR); Christelle Nguyen, Paris (FR); Claire Mangeney, Villejuif (FR); Olivier Piot, Cormontreuil (FR)

(73) Assignees: ASSISTANCE PUBLIQUE-HOPITAUX DE PARIS, Paris (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR); UNIVERSITE DE REIMS CHAMPAGNE-ARDENNE, Reims (FR); UNIVERSITE PARIS CITE, Paris (FR)

( * ) Notice: Subject to any disclaimer, the term of this patent is extended or adjusted under 35 U.S.C. 154(b) by 910 days.

(21) Appl. No.: 17/762,760

(22) PCT Filed: Sep. 23, 2020

(86) PCT No.: PCT/EP2020/076577
§ 371 (c)(1),
(2) Date: Mar. 23, 2022

(87) PCT Pub. No.: WO2021/058570
PCT Pub. Date: Apr. 1, 2021

(65) Prior Publication Data
US 2022/0349902 A1      Nov. 3, 2022

(30) Foreign Application Priority Data
Sep. 23, 2019      (EP) ..................................... 19306176

(51) Int. Cl.
*G01N 33/68* (2006.01)
*G01N 21/65* (2006.01)
*G01N 33/543* (2006.01)

(52) U.S. Cl.
CPC ....... *G01N 33/6887* (2013.01); *G01N 21/658* (2013.01); *G01N 33/54346* (2013.01); *G01N 33/54373* (2013.01); *G01N 2800/10* (2013.01)

(58) Field of Classification Search
CPC ......... G01N 33/6887; G01N 33/54346; G01N 33/54373; G01N 21/658; G01N 2800/10
See application file for complete search history.

(56) References Cited

U.S. PATENT DOCUMENTS

2007/0082409 A1      4/2007      Morris et al.

OTHER PUBLICATIONS

Bocsa, et al. "Knee osteoarthritis grading by resonant Raman and surface-enhanced Raman scattering (SERS) analysis of synovial fluid." Nanomedicine: Nanotechnology, Biology, and Medicine. vol. 20. May 11, 2019. 10 pages.
(Continued)

*Primary Examiner* — Kathryn Elizabeth Limbaugh
(74) *Attorney, Agent, or Firm* — Tucker Ellis LLP

(57) ABSTRACT
The invention relates to a SERS method for analyzing a biological sample, the method comprising the following step of: a. obtaining a biological sample which is viscous bio-fluid, b. depositing at least one droplet of the biological sample onto a microscope slide, and drying the droplet, c. depositing a drop of an aqueous dispersion of metallic
(Continued)

The Inverse Method Protocol

Figure 1:
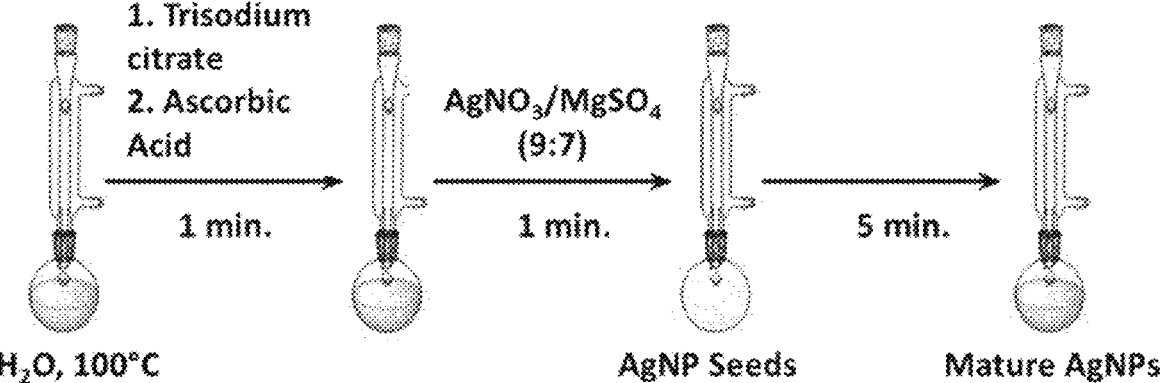

A          B nanoparticles above the droplet dried in step b), to have a dense distribution of nanoparticles on the surface of the dried droplet and to obtain a SERS-activated biological sample, d. drying the SERS-activated biological sample, e. irradiating the SERS-activated biological sample using a light source to obtain a SERS spectrum, and f. collecting the SERS spectrum.

12 Claims, 5 Drawing Sheets

(56)                    References Cited

OTHER PUBLICATIONS

Bonifacio, et al. "Label-free surface-enhanced Raman spectroscopy of biofluids: fundamental aspects and diagnostic applications." Analysis of Bioanalytical Chemistry. 2015. vol. 407., No. 27, pp. 8265-8277.
Li, et al. "Noninvasive prostate cancer screening based on serum surface-enhanced Raman spectroscopy and support vector machine." Applied Physics Letters. 2014. vol. 105., No. 9. 4 pages.
Premasiri, et al. "Surface Enhanced Raman Scattering of Whole Human Blood, Blood Plasma and Red Blood Cells: Cellular Processes and Bioanalytical Sensing." Journal of Physical Chemistry Part B. Aug. 9, 2012. vol. 116, No. 31. pp. 9376-9386.
Brozek-Pluska, et al. "Surface-Enhanced Raman Spectroscopy Analysis of Human Breast Cancer via Silver Nanoparticles: An Examination of Fabrication Methods." Journal of Spectroscopy. vol. 2018, Article ID 4893274. 8 pages.
International Search Report and Written Opinion in PCT/EP2020/076577 dated Dec. 21, 2020 (15 pages).

1. Trisodium citrate
2. Ascorbic Acid 1 min.

$AgNO_3/MgSO_4$ (9:7)

1 min.

5 min.

$H_2O$, 100°C

AgNP Seeds

Mature AgNPs

The Inverse Method Protocol

A

B

1μm

SERS METHOD FOR ANALYZING A VISCOUS BIOFLUID

FIELD OF THE INVENTION

The present invention relates to the field of the diagnosis of disease, particularly joint diseases. The invention relates to a SERS method for analyzing a biological sample which is a viscous biofluid, particularly a synovial fluid, for diagnosing, prognosing a joint disease.

BACKGROUND OF THE INVENTION

Biofluids are produced during biological functions and comprised a wide range of components such as small organic molecules, nutrients, cells, proteins, microbes, and genetic sequences. For example, blood is a commonly collected and studied biofluid for assessing a person's disease risk before it manifests itself, for diagnosing a disease after its onset, or for staging the disease's development and/or remission over time. Blood is not only easy to collect but it drains side products from many body systems, making it an ideal sample for detecting diseases.

However, other biofluids can still be useful for disease diagnosis because they give very specific information. In particular, synovial fluid (SF) is highly informative about the health of the musculoskeletal system because it is confined in the joints, but difficult to access. Today, clinicians use the presence of monosodium urate monohydrate (MSUM) and calcium pyrophosphate crystals (CPPD) in the fluid as an indicator of joint diseases.

Synovial fluid is composed of blood plasma dialysate with a molecular composition that includes hyaluronic acid, proteoglycan 4, surface-active phospholipids, and all the proteins found in blood plasma. As joint diseases like rheumatism and osteoarthritis develop, the composition and concentration of synovial fluid is marked by compositional changes, but there is, to date, no established biomarker signature to define this disease progression. Finding this biomarker signature is believed to be one method for early diagnosis of joint diseases, which can allow for treatment of the disease before the joint becomes too damaged.

Thus, analysis of biomarkers in biofluids via vibrational spectroscopies can reveal specific spectroscopic signatures that are akin to molecular "fingerprints" of the disease. Spectroscopic detection limits are among the many challenges of identifying biomarker signatures. Because biofluids are complex mixtures, key biomarkers might exist in such low concentrations with respect to the other biofluid components that their spectroscopic signals are masked by the more dominant signals. Therefore, the ideal spectroscopic technique for identifying biomarker signatures in biomedical research would be able to detect multiple components at one time, be sensitive even to low concentrations of molecules, and, for the eventual clinical application, be easy to examine after sample collection from minimally invasive procedures. Raman spectroscopy and surface-enhanced Raman spectroscopy (SERS) are among the possible spectroscopic techniques that could be applied to this search for biomarker signatures.

Raman spectroscopy is a sensitive vibrational spectroscopy that probes the intramolecular vibrations of a sample when irradiated with light. This technique could be used to observe vibrational, rotational, and other low-frequency modes in a system. Raman spectroscopy is commonly used in chemistry to provide a structural fingerprint by which molecules can be identified. As opposed to other vibrational spectroscopies, Raman spectroscopy has several advantages for studying biological samples. One of the most primordial is that water, the solvent of life, is a weak Raman scatterer. But Raman spectroscopy has several disadvantages too. Indeed, Raman scattering is a relatively weak process, the amount of scattered Raman photons being quite small. Consequently, Raman is not sensitive enough to obtain all information required to analyze biological sample, in particular in the early diagnosis of joint disease. Thus, there is a need to have a method that will give more information on this type of biological sample, by enhancing the collected Raman signals.

Surface-enhanced Raman spectroscopy (SERS) can hold such promises by combining the rich chemical fingerprint information based on Raman spectroscopy and a high sensitivity due to the local field enhancement offered by optically resonant metal nanoparticles. Briefly, a nanostructured surface is used to enhance the Raman scattering of an analyte by both a chemical factor and an electromagnetic factor, directly related to the properties of the analyte and the nanostructured surface, preferably noble metal nanoparticles. When incident light interacts with the noble metal nanoparticles, an optical phenomenon called localized surface plasmon resonance (LSPR) occurs. The LSPR effect results in an intense and highly localized electromagnetic field around the nanoparticle surface, and it also allows for increased photon scattering that can be exploited in SERS for increased sensitivity. The SERS effect is maximized by exciting a roughened surface of nanoparticles at the precise wavelength of the surface plasmon. In order to observe the SERS effect on biological samples, this excited, roughened, nanostructured surface needs to come in contact with the analyte of interest without denaturing it.

In particular, the U.S. Ser. No. 11/521,295 describes a SERS method for measuring cartilage condition markers. In particular, the biological sample was deposited on the SERS substrate. The results obtained with this method do not allow for recording intense SERS signals for obtaining an early diagnosis of joint disease. Moreover, a pretreatment process, typically using trichloric acid, to induce protein precipitation, was necessary to reveal the Raman peaks of hyaluronic acid, used as a biomarker. This strategy thus requires multiple steps to analyze the SF by SERS, which is time-consuming and may lead to some denaturation of the native SF samples. Moreover, it does not provide a complete overview of the SERS signature of SF, which may decrease the wealth of information available by SERS.

Today, joint diseases are diagnosed through radiographic and physical examination, but these methods lack sensitivity for very early diagnosis. Other means for monitoring pathophysiological changes in the joint is to analyze the SF because of its direct and intimate relationship with synovial membrane, articular cartilage and other tissue types of knee joint. The earliest pathophysiological changes in a degenerative knee joint could be detected in SF. Although visual examination has been used by rheumatologists for the past 50 years to analyze SF, they provide limited quantitative data and fail to describe the biochemical and chemical changes, such as alterations in protein composition and proteomic profile undergone by SF in joint diseases. Therefore, the development of new approaches to obtain measurements that reflect the entire SF chemical or biological profile is an important challenge for the early diagnosis of joint disease. To date, few publications have shown that Raman spectroscopy can be used to detect changes in SF from patients with joint diseases. For example, the Raman band intensity ratios were shown to vary significantly in spectra collected from SF in patients with radiological evidence of osteoarthritis damage. Other publications focused on the Raman analysis of crystals extracted from SF. However, the Raman signals have low intensity and the clinical applications of this technique have been limited and is not really satisfying. Therefore, the optimization and development of novel analytical methods and protocols for rapid, inexpensive, and on-site detection and monitoring of entire SF still remains a challenge.

Despite studies to identify a biomarker signature in synovial fluid for early diagnosis, disease staging and prognosis, no biomarker signature, preferably spectral signature has yet been identified. Thus, the identification of biomarker signature remains challenging.

SUMMARY OF THE INVENTION

Up to now, it was of common knowledge in the art that SERS method for analyzing viscous biofluid is not satisfying because the resulting spectra had the same features and same intensity as a Raman spectrum (i.e. without using nanoparticles) thereby depriving of any interest the use of such a complex method as SERS for analyzing viscous fluids. Inventors have developed a method that allows fully exploiting sensitivity potential of SERS for analyzing biological samples which are viscous biofluids.

More particularly, inventors surprisingly found that the SERS technique they developed can be used for revealing intense Raman signature of synovial fluid for the classification of joint diseases. Obtaining an optical signature with SERS spectra allows to classify diseases, severity of disease, early diagnosis. Early diagnosis would prevent irreversible damage that is very common in this type of pathology. These lesions are caused by an often-late diagnosis which therefore does not allow a rapid management and thus leads to irreversible damage to the patient.

In a first aspect, the invention relates to a SERS method for analyzing a biological sample, the method comprising the step of:

a. obtaining a biological sample which is a viscous biofluid, b. depositing at least one droplet of the biological sample onto a microscope slide, and drying the droplet, c. depositing a drop of an aqueous dispersion of metallic nanoparticles above the droplet dried in step b), to have a dense distribution of nanoparticles on the surface of the dried droplet and to obtain a SERS-activated biological sample, d. drying the SERS-activated biological sample, e. irradiating the SERS-activated biological sample using a light source to obtain a SERS spectrum, and f. collecting and analyzing the SERS spectrum.

In a preferred embodiment, the metallic nanoparticles used in the method of the invention are colloidal metallic nanoparticles dispersed in water, preferably colloidal silver nanoparticles.

In a particular embodiment, the invention relates to a SERS method for analyzing a biological sample which is a viscous biofluid, the method comprising the step of:

a. depositing at least one droplet of the biological sample onto a microscope slide, and drying the droplet, b. depositing a drop of an aqueous dispersion of metallic nanoparticles above the droplet dried in step a), to have a dense distribution of nanoparticles on the surface of the dried droplet and to obtain a SERS-activated biological sample, c. drying the SERS-activated biological sample, d. irradiating the SERS-activated biological sample using a light source to obtain a SERS spectrum, and e. collecting and analyzing the SERS spectrum.

In a second aspect, the invention relates to a method for diagnosing or identifying, in a biological sample, a joint disease, wherein the method comprises the steps of:

a. depositing at least one droplet of said biological sample onto a microscope slide, and drying the droplet, b. depositing a drop of an aqueous dispersion of metallic nanoparticles above the droplet dried in step b), to have a dense distribution of nanoparticles on the surface of the dried droplet and to obtain a SERS-activated biological sample, c. drying the SERS-activated biological sample, d. irradiating the SERS-activated biological sample using a light source to obtain a SERS spectrum, and e. collecting and analyzing the SERS spectrum.

In a particular embodiment, the invention relates to an in vitro method for diagnosing or identifying, in a biological sample which is a viscous biofluid, a joint disease, wherein the method comprising the step of:

a. depositing at least one droplet of said biological sample onto a microscope slide, and drying the droplet, b. depositing a drop of an aqueous dispersion of metallic nanoparticles above the droplet dried in step a), to have a dense distribution of nanoparticles on the surface of the dried droplet and to obtain a SERS-activated biological sample, c. drying the SERS-activated biological sample, d. irradiating the SERS-activated biological sample using a light source to obtain a SERS spectrum, and e. collecting and analyzing the SERS spectrum.

In a preferred embodiment, the method further comprises a step for the construction of a supervised classification model on a library of SERS spectra of joint diseases in order to blindly predict the disease of new patients from the SERS spectra acquired on their Synovial Fluid sample.

Accordingly, the step of analyzing the SERS spectrum comprises additional sequential steps:

i. a pre-processing step for correcting spectral interferences of said SERS spectrum and normalize them, ii. a step of selecting of features and/or reducing data to identify discriminant wavenumbers, iii. a step of construction of a supervised classification model using machine learning approaches for automatic prediction of new samples.

In another aspect, the invention relates to a kit for analyzing a biological sample comprising a Raman device, a SERS substrate, characterized in that the kit further comprising a computing device configured to determine or identify a joint disease in a biological sample based on the spectral content information. In a preferred embodiment, the kit comprising a SERS substrate, wherein the SERS substrate is deposited onto the biological sample.

In a more preferred embodiment, the kit comprises a computing device being configured according to the method of the invention described above.

In another preferred embodiment, the kit comprises a computing device being configured to execute the sequential steps (i. to iii.) described above.

In another aspect, the invention relates to a use of the kit for diagnosing or identifying a joint disease in a subject. More particularly said kit is adapted for implementing any of the methods of the invention as exposed herein.

The invention is particularly suited to identify a biomarker signature for early diagnosis of joint disease and classify them.

LEGEND OF DRAWING

Other advantages and characteristics of the disclosed method of the present invention will become apparent from reading the description, illustrated by the following figures, where:

FIG. 1. represents the AgNPs synthesis pathway according to one embodiment of the invention.

Figure 2:
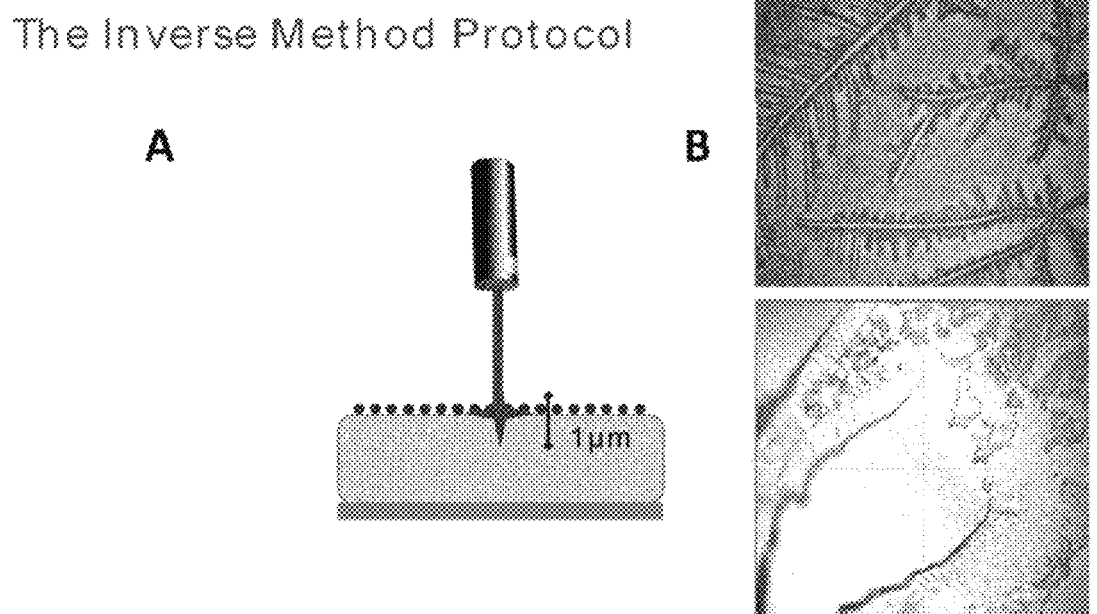

FIG. 2. represents the inverse method protocol consisting to add silver nanoparticles on top of the dried drop of SF. On the right side, figures represent a dried SERS substrate appearance of the synovial fluid droplet.

Figure 3:
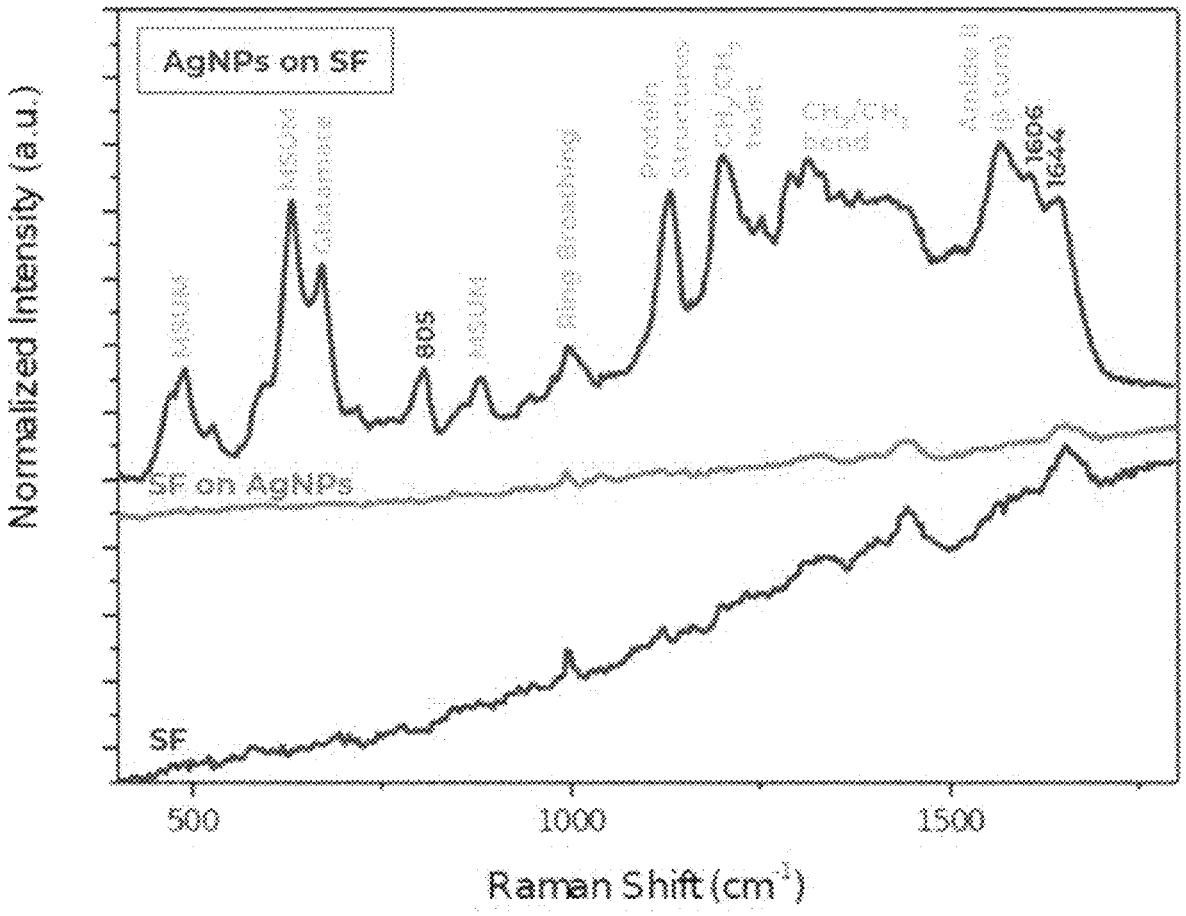

FIG. 3. represents a comparison of the Raman spectra from the unadulterated synovial fluid (SF), synovial fluid deposited on dried AgNPs (SF on AgNPs), and the SERS spectra obtained by the Inverse Method with AgNPs (AgNPs on SF).

Figure 4:
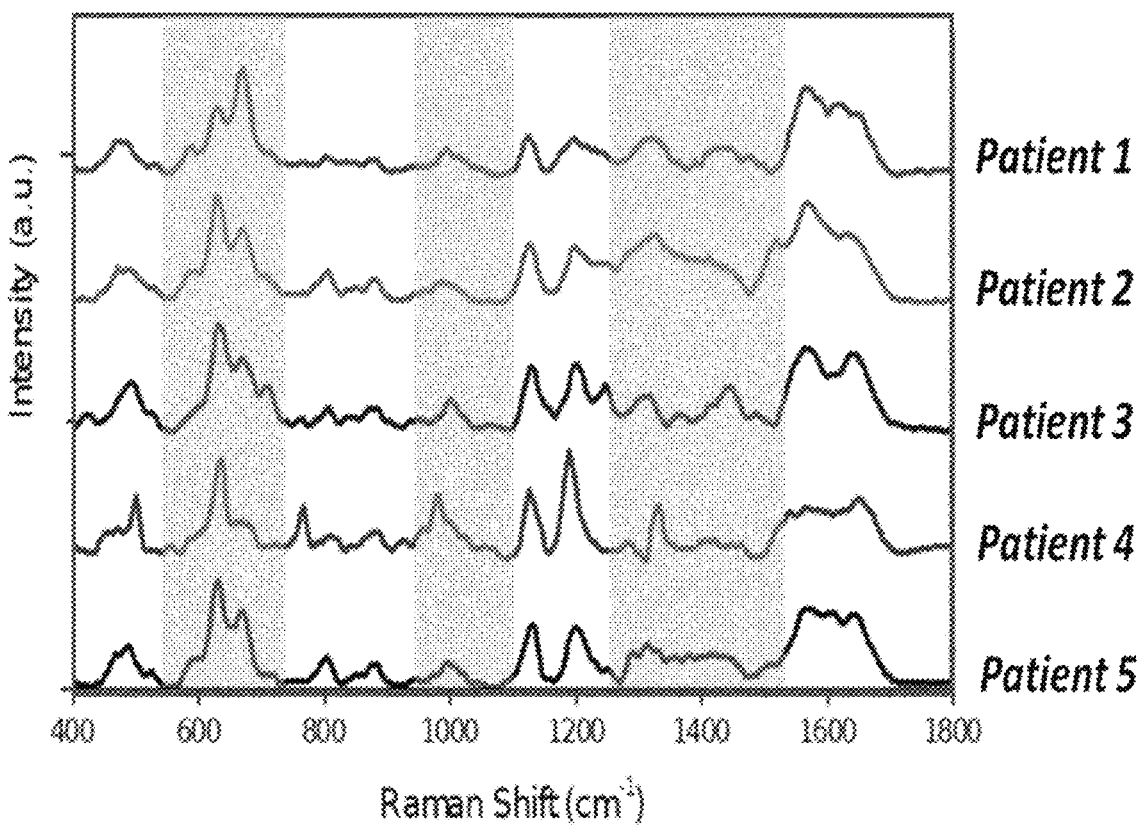

FIG. 4. represents the SERS spectra of SF collected from 5 different patients, confirming the high reproducibility of the analysis and revealing minor differences which will be used to classify the various types of diseases.

Figure 5:
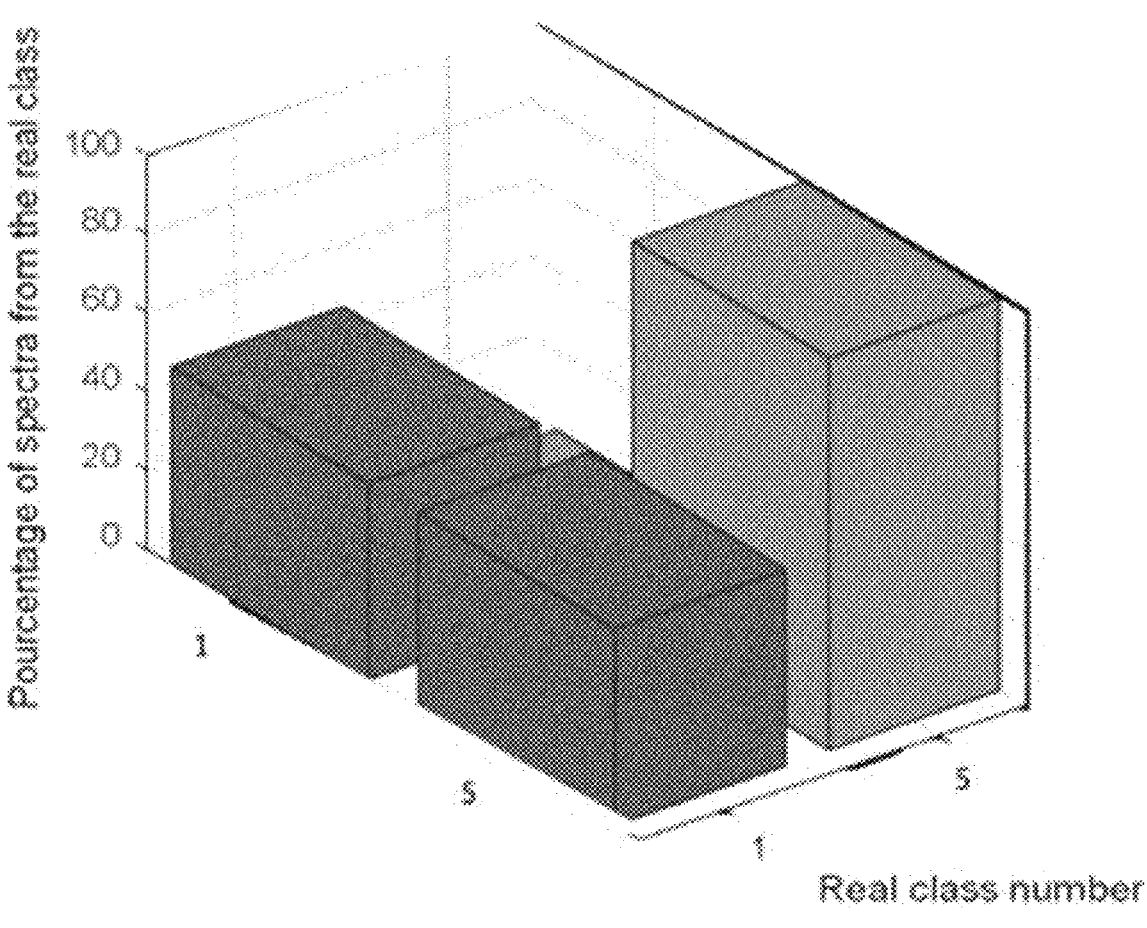

FIG. 5. represents the statistical analysis of the Raman spectra of 2 different groups of patients with Gonarthrosis (group 1) or Rheumatoid arthritis (group 5), demonstrating that the method is not efficient enough to accurately discriminate SF samples from patients with different diseases.

Figure 6:
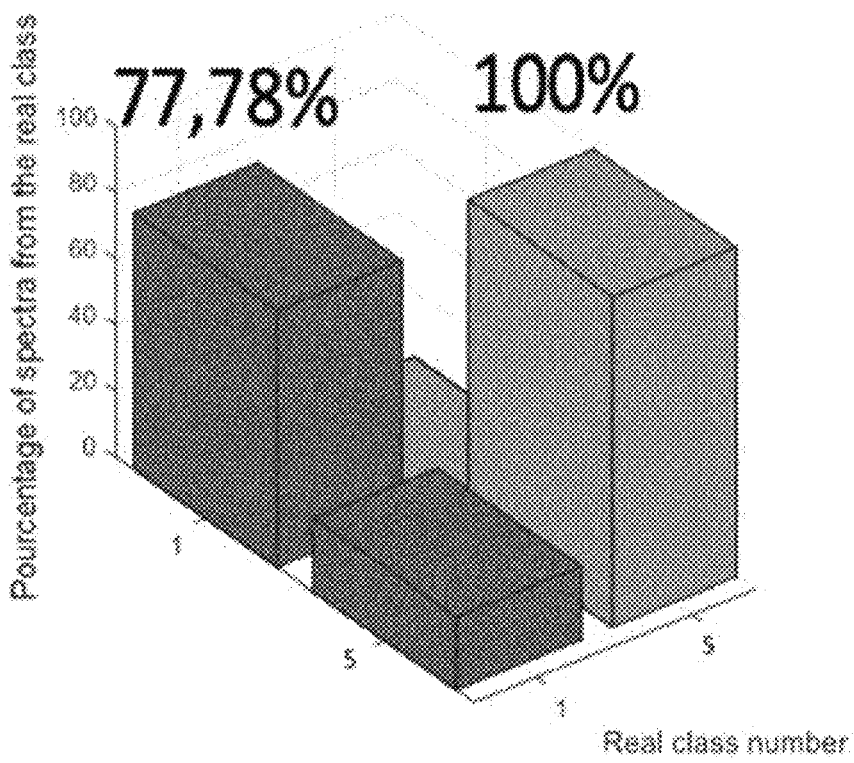
Figure 6:
Figure 6:
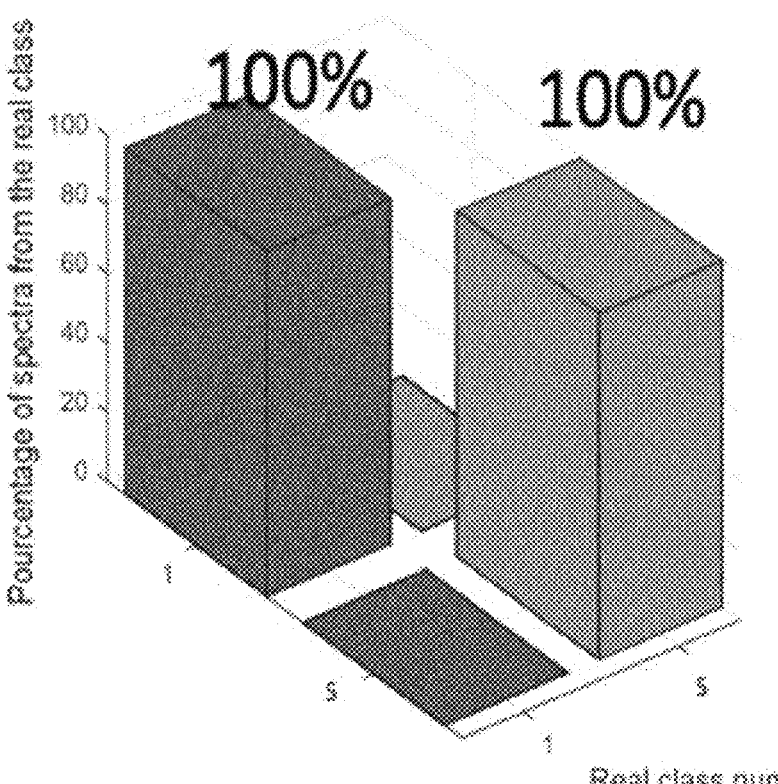

FIG. 6. displays the statistical analysis of the SERS spectra of 2 different groups of patients with Gonarthrosis (group 1) or Rheumatoid arthritis (group 5), demonstrating that the spectral differences revealed by the method are highly informative for the statistical discrimination between the two groups.

DETAILED DESCRIPTION OF THE INVENTION

As intended herein, the term "comprising" has the meaning of "including" or "containing", which means that when an object "comprises" one or several elements, other elements than those mentioned may also be included in the object. In contrast, when an object is said to "consist of" one or several elements, the object cannot include other elements than those mentioned.

According to the invention, the terms "subject", "individual", and "patient" are used interchangeably herein and refer to a mammal affected or likely to be affected of joint diseases. Subjects are preferably humans.

In a first aspect, the invention relates to a SERS method for analyzing a biological sample, the method comprising the step of:
   a. obtaining a biological sample which is viscous biofluid,
   b. depositing at least one droplet of the biological sample onto a microscope slide, and drying the droplet,
   c. depositing a drop of an aqueous dispersion of metallic nanoparticles above the droplet dried in step b), to have a dense distribution of nanoparticles on the surface of the dried droplet and to obtain a SERS-activated biological sample,
   d. drying the SERS-activated biological sample,
   e. irradiating the SERS-activated biological sample using a light source to obtain a SERS spectrum, and
   f. collecting and analyzing the SERS spectra.

In a particular embodiment, the invention relates to a SERS method for analyzing a biological sample which is a viscous biofluid, the method comprising the step of:
   a. depositing at least one droplet of the biological sample onto a microscope slide, and drying the droplet, b. depositing a drop of an aqueous dispersion of metallic nanoparticles above the droplet dried in step a), to have a dense distribution of nanoparticles on the surface of the dried droplet and to obtain a SERS-activated biological sample,
   c. drying the SERS-activated biological sample,
   d. irradiating the SERS-activated biological sample using a light source to obtain a SERS spectrum, and
   e. collecting and analyzing the SERS spectrum.

As intended herein, the term "dense distribution" refers to the surface concentration of nanoparticles on the drop of synovial fluid. According to the invention, the dense distribution corresponds to a surface concentration of nanoparticles of at least $10^{15}$ nanoparticles/m$^2$. Preferably according to the invention, the surface concentration of nanoparticles is at least from $10^{15}$ nanoparticles/m$^2$ to $10^{17}$ nanoparticles/m$^2$, preferably, $5 \cdot 10^{15}$ nanoparticles/m$^2$ to $8 \cdot 10^{16}$ nanoparticles/m$^2$, more preferably $8 \cdot 10^{15}$ nanoparticles/m$^2$ to $6 \cdot 10^{16}$ nanoparticles/m$^2$, more preferably $10^{16}$ to $4 \cdot 10^{16}$ nanoparticles/m$^2$. In a more preferred embodiment, the optimal surface concentration of nanoparticles is $3 \cdot 10^{16}$ nanoparticles/m$^2$ or $5 \times 10^{-8}$ mol/m$^2$.

In a preferred embodiment of the invention, the step of irradiating the SERS-activated biological sample using a light source to obtain a SERS spectrum, and the step of collecting and analyzing the SERS spectrum are repeated at least once, at least twice, at least three times, at least four times, at least five times, at least six times, at least seven times, at least eight times, at least nine times, at least ten times and more, preferably at least ten times to obtain SERS spectra. Further, said spectra are analyzed together, in other words said spectra are then jointly analyzed.

Typically, said methods involve the use of biological sample obtained from the patient. As used herein the term "biological sample" encompasses a variety of sample types obtained from a subject and can be used in a diagnostic or monitoring assay. Biological samples include but are not limited to synovial fluid and other liquid samples of biological origin. For example, biological samples include synovial fluid collected from an individual suspected of having a joint disease.

As discussed above, the surface-enhanced Raman spectroscopy (SERS) is one of technique that may be used to detect biological information of joint disease. Usually, with the SERS method, the biological sample to be analyzed is placed on a SERS substrate. A SERS substrate may be a substrate having an array of metallic, for example gold, platinum, silver, titanium, zinc, copper, or metal coated structures that when irradiated give an optical phenomenon called localized surface plasmon resonance (LSPR). This effect allows to obtain precious information in said biological sample.

In a preferred embodiment of the invention, the SERS substrate is composed of metallic nanoparticles, more preferably colloidal metallic nanoparticles. Advantageously, the colloidal metallic nanoparticles comprise silver, more preferably nanoparticle is an aqueous dispersion of colloidal silver nanoparticles (AgNPs).

Advantageously, spherical silver colloids have easy and scalable synthesis, long shelf-life and dispersion in water (a biologically relevant solvent). Additionally, AgNPs have surface plasmon resonance properties that allow them to interact with visible light. The AgNPs were synthesized in boiling water without purification (FIG. 1). The reducing agents, trisodium citrate and ascorbic acid, were added to the reactional medium first, followed by a solution of silver nitrate and magnesium sulfate. The beginning of the reduction was indicated by a color change from clear to yellow, and the completion of the reaction was indicated by a second color change from yellow to orange.

Further, the AgNPs were characterized by pH potentiometry, UV-vis spectroscopy, Raman spectroscopy, and scanning electron microscopy (SEM). The pH of the colloid solution was determined to be nearly neutral at 6.5 pH units, which meant that it was compatible with the biological samples. Furthermore, the plasmon resonance wavelength was determined to be 413 nm using UV-vis spectroscopy, where the orange solution had an absorption of nearly 3 absorbance units.

Additionally, in Raman spectroscopy, several very intense peaks were observed at 744, 843, 957, 1070, 1139, 1156, 1290, 1321, 1380, 1446, 1493, 1536 cm$^{-1}$. These peaks were assigned to the ascorbate, citrate, nitrate, and sulfate anions that surrounded and stabilized the AgNPs. Using SEM, the nanoparticles were found to have a more or less spherical morphology, and they varied in size from 20 nm to 100 nm.

In another embodiment, the method of the invention is intended to analyze biological sample, which is viscous biofluid. Advantageously, a viscous biofluid can be analyzed according to the method of the present, preferably the viscous biofluid is a synovial fluid previously obtained from patient. According to a preferred embodiment of the invention, the viscous biofluid that can be used in the method to analyze has a viscosity comprised between 0.6 to 14 poise.

Using a traditionally SERS method for analyzing viscous biofluid is not satisfying because the resulting spectra had the same features and same intensity as a Raman spectrum. The samples gave the same Raman signature as the viscous biofluid alone, indicating that this protocol was not suitable for SERS of viscous biofluid.

To remedy this disadvantage, inventors surprisingly found that depositing metallic nanoparticles above the droplet of biological sample which is a viscous biofluid previously dried allows to have a dense distribution of nanoparticles on the surface of the dried droplet and to obtain a SERS-activated biological sample, and finally obtaining a satisfying spectrum. This aspect will be described in more detail below in "the inverse method" part (FIG. 2).

In an embodiment of the invention, the method requires a "control" sample to have a reference for comparison with the SERS results. In a particular embodiment, said "control" sample is an unadulterated Synovial Fluid Sample.

Slides were prepared using drop deposition, as described by Esmonde-White and coworkers. In this method, at least 2 μL of centrifuged synovial fluid was deposited onto the surface of a clean microscope slide and left to dry overnight. The resulting drops were marked by two regions whose morphologies were distinguishable in confocal microscopy; the center was found to have fern-like crystals whereas the edge was found to have a crown-like aggregation of tiny crystals. The heterogeneous morphologies were nicknamed as the drop center and the "crown edge" to differentiate them. Additionally, the two regions could be distinguished by a difference in the Raman signature peak intensities: the crown edge was found to have more intense peaks than the drop center. Furthermore, the peak shifts varied slightly between the two regions. Because of these minor differences, each unadulterated synovial fluid sample was analyzed for a total of ten times, with five measurements taken in the sample's drop center and five measurement taken in the crown edge. The results from each region were then averaged separately to give two spectra that represented the components in synovial fluid.

These Raman shifts were assigned according to the literature (Table 1). The results indicated that the Raman biosignature of synovial fluid was characterized by protein structures as well as some organic content.

TABLE 1

| Assignments for the Raman signature of unadulterated synovial fluid | | |
|---|---|---|
| Raman Shift (cm$^{-1}$) | Band Assignment | Component |
| 995 | Ring breathing | Protein, Phe residue |
| 1135 | C—C stretch | Protein structures |
| 1224 | Amide III, random coil | Protein structures and other organic content |
| 1328 | CH$_2$/CH$_3$ wag | Organic content |
| 1655 | Amide I, α-helix | Protein structures |

Further this first step which requires the "control" sample, the biological sample is prepared according to traditional methods for SERS.

Biological samples are prepared for SERS studies by either (1) depositing a droplet of the analyte onto a SERS substrate, consisted of a gold nanostructured surface deposited on indium tin oxide (ITO) and leaving it to dry or (2) by mixing gold or silver NPs with the unadulterated analyte and depositing a droplet of the mixture onto a microscope slide. Both methods were attempted but neither resulted in a SERS spectrum. Rather, the resulting spectra had almost the same features and same intensity as the control.

Inventors identified that the viscosity of the synovial fluid had a role in why a SERS signature could not be obtained using these methods. Being a very viscous biofluid, synovial fluid dries as a relatively thick droplet on the SERS surface, making it difficult to access the interface of the analyte and the SERS substrate by simply focusing the microscope on the sample. Trying to obtain a SERS signal by manually adjusting vertical position of the microscope stage while the laser was active until reaching the SERS-active interface between the analyte and the SERS substrate, is time-consuming. Furthermore, prolonged exposure to the laser while adjusting its position risks not only photobleaching the signal, but also burning the biological sample due to the laser irradiation and the photothermal effect of nanoparticles.

Therefore, it was necessary to develop an alternative means of enhancing the Raman signature in SERS. Inventors tried first, a method for diluting the synovial fluid so that the drop would be less thick when it dried on the surface. But this method was disfavored because of the concern that diluting the synovial fluid denatured some of the proteins. This was observed by certain spectral differences between the Raman signatures of the dilute and unadulterated synovial fluid. Accordingly, this method is not possible for diagnostic purposes from a biological sample which is a viscous fluid, more particularly from synovial fluid which can be denatured.

As previously evoked to remedy this disadvantage, the inventors tried to add the SERS-active nanoparticles on top of the dried drop of synovial fluid (FIG. 2). The inventors surprisingly found that the deposition of metallic nanoparticles above the dried SF droplet allows to have a dense distribution of nanoparticles on the surface of the SF dried sample resulting in a SERS-activated biological sample which can be analyzable by SERS (FIG. 3). Said method is called "Inverse Method" in the context of the invention.

The Inverse Method

The inventors developed the "inverse method," where the order of the drop deposition was reversed. Rather than depositing the synovial fluid on a dry SERS-active surface, the chosen SERS-active substrates were deposited onto dried droplets of synovial fluid (FIG. 2). On the right side, figures represent a dried SERS substrate appearance of the synovial fluid droplet.

Different SERS substrates were tested in this manner, AuNPs alone, and AgNPs alone. Better results were obtained with AgNPs alone. These nanomaterials were all dispersed in water and were, therefore, much more fluid than the analyte. As such, it was hypothesized that they would dry as a thin layer on its surface, giving easy access to the substrate-analyte interface.

In each case, the dried SERS substrate changed the appearance of the synovial fluid droplet, but without denaturating the synovial fluid sample. The crystals in the drop center grew, whereas the crown edge became much less pronounced. This indicates that the nanoparticles interacted with the synovial fluid, giving them access to the molecular components in the biofluid.

Inverse Method with Colloidal AgNPs

Finally, colloidal AgNPs were found to be successful enhancers for the synovial fluid spectroscopic signature using the inverse method. With this combination, the synovial fluid was successfully characterized by a signal that was (1) much more intense than the Raman signal obtained from unadulterated synovial fluid, (2) more enhanced than the signal obtained from the traditional method of depositing a droplet of the synovial fluid on top of a dried droplet of AgNPs, and (3) different from the Raman shifts of the AgNPs on their own (FIG. 3). This indicated that a SERS signal was successfully achieved by the combination of the inverse method with silver nanoparticles.

In a preferred embodiment, the step of depositing at least one droplet of the biological sample onto a microscope slide, and especially the step of drying the droplet is essential for obtaining a SERS spectrum which could be interpretable and clear enough to analyze said spectrum. The step of drying according to the invention, allows to obtain a migration of the SERS-active nanoparticles, such as AgNPs, at the surface of the biological sample and thus, have formation of AgNPs aggregates promoting the SERS effect.

The inverse method enhanced the intensity of several Raman peaks, assigned to different protein structures (Table 2).

TABLE 2

| Assignments for the SERS peaks that were revealed by the inverse method and not the dilution method. | | |
|---|---|---|
| Raman Shift | Peak Assignment | Synovial Fluid Component |
| 623 | Phenylalanine/Tyrosine content | Protein structure |
| 792 | C—O—C Stretching of collagens | Collagen Type II |
| 869 | Tyrosine interactions | Protein structure |
| 1123 | C—C stretch | Protein/Hyaluronic acid |
| 1197 | CH$_2$ twist | Protein/Hyaluronic acid |
| 1238 | Amide III, random coil | Protein |

In another embodiment of the invention, the SERS method for analyzing a biological sample, wherein the step of analyzing the SERS spectrum or spectra comprises the following sequential steps:

i. a pre-processing step for correcting spectral interferences of said SERS spectrum and normalize them, ii. a step of selecting features and/or reducing data to identify discriminant wavenumbers.

Signature Reproducibility with the Inverse Method of 5 Different Patients (FIG. 4)

Because the dilution method could not provide intense SERS signatures of the SF samples, it the inverse method is be more effective for testing a large number of samples. To test the reproducibility of the inverse method, a number of synovial fluid samples were collected from patients who were being treated at the Pôle Osteo-articulaire of the Institut Cochin for either osteoarthritis or rheumatism (Patient 1, 2, 3, 4 and 5). These samples were prepared according to the inverse method protocol described above and studied in SERS.

The biosignatures for five different samples were found to have many of the same features, although the peak intensities varied slightly between the samples (FIG. 4). While this indicated that using the inverse method of preparation with AgNPs is reliable and efficient, it also indicated that a much deeper analysis is necessary to understand the relationship between the changing peaks and the underlying diseases.

In another preferred embodiment, the step of drying the droplet of the biological sample is realized during several hours before depositing the nanoparticles onto the top of the dried biofluid sample.

Accordingly, the invention relates to a method for diagnosing or identifying, in a biological sample which is a viscous biofluid, a joint disease. In the context of the invention, the joint disease is preferably rheumatic or a musculoskeletal disease. Rheumatic and musculoskeletal diseases affect a quarter of all people in the European Union. They are the first cause of sick leave and premature retirement worldwide. Therefore, these diseases have a huge economic burden on global healthcare systems. In Europe, public spending totals over €200 billions per year. Current diagnostic methods usually do not catch the disease until it is in advanced stages when joint damage may already have occurred. A method for early diagnosis could open a window of opportunity for preventing or reducing permanent joint damage.

Thus, the invention relates to a method for diagnosing or identifying in a biological sample which is viscous biofluid, a joint disease, wherein the method comprising the step of:

a. obtaining a biological sample which is viscous biofluid, b. depositing at least one droplet of the biological sample onto a microscope slide, and drying the droplet, c. depositing a drop of an aqueous dispersion of metallic nanoparticles above the droplet dried in step b), to have a dense distribution of nanoparticles on the surface of the dried droplet and to obtain a SERS-activated biological sample, d. drying the SERS-activated biological sample, and irradiating them using a light source to obtain a SERS spectrum, and e. collecting and analyzing the SERS spectrum.

In a particular embodiment, the invention relates to an in vitro method for diagnosing or identifying in a biological sample which is viscous biofluid, a joint disease, wherein the method comprising the step of:

a. depositing at least one droplet of the biological sample onto a microscope slide, and drying the droplet, b. depositing a drop of an aqueous dispersion of metallic nanoparticles above the droplet dried in step a), to have a dense distribution of nanoparticles on the surface of the dried droplet and to obtain a SERS-activated biological sample, c. drying the SERS-activated biological sample, and irradiating them using a light source to obtain a SERS spectrum, and d. collecting and analyzing the SERS spectrum.

In a preferred embodiment, the method further comprising a step for the construction of a supervised classification model on a library of SERS spectra of joint diseases in order to blindly predict the joint disease of new patients from the SERS spectra acquired on their SF.

More particularly, the step of analyzing the SERS spectra d) comprises additional sequential steps:

i. a pre-processing step of correcting the spectral interferences and normalizing them, ii. a step of selecting of features and/or reducing data to identify discriminant wavenumbers, iii. a step of constructing a supervised classification model using machine learning approaches for automatic prediction of new samples.

In first, the analysis process of SERS spectra requires a pre-processing step for correcting the spectral interferences and normalize them. Indeed, the main spectral interference is a baseline (a low frequency signal superimposed to the Raman signature) due to the biological sample autofluorescence. Then, variations of sample thickness, laser spot focus and optical path length from one sample to another result in variation of the intensity range of the acquired vibrational spectra, which can be corrected by a normalization step. Several methods exist in literature to correct these two effects. However, Extended Multiplicative Signal Correction (EMSC) has been used in order to simultaneously correct them, hence limiting the propagation of estimation errors, by considering the mean dataset spectrum as the reference spectrum and a fourth-degree polynomial function modeling the baseline.

Secondly, a step of feature selection/extraction and/or data reduction is required to identify discriminant wavenumbers and/or components. Here, Principal Component Analysis (PCA) was performed in order to extract uncorrelated components which explain most of the variance contained in the spectral data. However, before PCA application, the spectral data were mean centered in order to get free from the mean data spectrum which predominantly contributes to the data variance. Then, the resulting data were normalized using Standard Normal Variate (SNV) in order to have zero-mean and unit-variance spectra. Finally, PCA was applied on these normalized data. The first four principal component scores were retained for the next step, but this number may vary in function of the studied biological sample type, and its choice can be integrated into the next step, using for example cross-validation and grid-search strategies.

Finally, a supervised classification model is constructed using machine learning approaches for automatic prediction of new samples. The classifier parameters can be optimized using cross-validation and grid-search strategies. Here, the data were separated into a training set composed of ⅔ of the spectra in order to train a model using Linear Discriminant Analysis (LDA). The remaining ⅓ of spectra was kept for the validation of the learned model.

Statistical Analysis of 54 SF Fluid Samples by Raman Spectroscopy and by SERS (FIGS. 5 and 6):

TABLE 3

| Different groups of patients used for statistical analysis of the Raman spectra (FIG. 5 and 6). | |
| --- | --- |
| Women, n (%) | 38 (70.4%) |
| Men, n (%) | 16 (29.6%) |
| Age, Average (SD) | 65.4 (14.3) |
| Disease, n (%) | |
| Gonarthrosis | 31 (57.4) |
| Rheumatoid arthritis | 12 (22.2) |
| Chondrocalcinosis | 5 (9.3) |
| Spondylarthropathy | 3 (5.6) |
| Drop | 1 (1.9) |
| Juvenile arthritis | 1 (1.9) |
| Arthritis non classified | 1 (1.9) |

For example, applied on the discrimination of 2 different groups of patients with Gonarthrosis (group 1) or Rheumatoid arthritis (group 5), this statistical analysis led to a model presenting an accuracy of 100% on the validation set (FIG. 6). To demonstrate the efficiency of the proposed methodology, this trained model was blindly applied to SERS spectra acquired on the SF of 15 other patients, resulting to an accuracy of 100% (FIG. 6). Further, to demonstrate the efficiency of the method according to the invention, this trained model was applied to Raman spectra acquired on the SF of same patients, demonstrating that the method is not efficient enough to accurately discriminate SF samples from patients with different diseases (FIG. 5).

Further aspects and advantages of the invention will be disclosed in the following examples, which should be considered illustrative.

EXAMPLE

I. Materials and Instrumentation

Reagent-grade chemicals and solvents were purchased from VWR, Sigma-Aldrich, and Alfa Aesa. All reagents were used as received.

The localized surface plasmon resonance of all colloidal samples was probed by UV-vis spectroscopy in the range of 300-800 nm using a Shimadzu UV-2700 spectrometer. Raman and SERS measurements were collected using a Horiba XploRA Plus spectrometer with either a 532 nm or 638 nm laser focused by a confocal microscope with a 100× objective. The spectrometer was calibrated using a silicon wafer. The nanomaterials were characterized by SEM. All SEM images were obtained with a Zeiss Merlin spectrometer equipped with a Cameca SX100 electron microprobe.

II. Biological Sample Preparation

A total of 43 samples were collected directly from patients in the Pole Osteo-articulaire of L'Institut Cochin in Paris. These samples were centrifuged at 3,500 rpm for 15 minutes, and the supernatant was transferred to a clean tube and shaken to have a homogeneous sample that was free of cells. Aliquots of 50 μL and 500 μL were measured and stored at −80° C. until needed for Raman or SERS studies.

III. Raman Spectroscopy and SERS Parameters

Laser light was coupled with a 1% filter and line-focused through a 100× objective. The grating was set to 600 (750 nm). All spectra were acquired using 10 accumulations of 3-second acquisition times.

IV. Data Manipulation Protocol

All data was treated using Origin Pro 8. Each spectrum was normalized individually before being averaged with the other spectra from either the drop center or crown edge of corresponding synovial fluid sample. At least five normalized spectra were averaged to give the so-called biosignature. The removing of the baseline can be done using Fityk.

V. SERS Substrate Synthesis (Colloidal AgNPs)

Adapted from Pazos-Perez et al. [17]

Using a Graham condenser column, 25 mL of distilled $H_2O$ was heated to boiling and stirred vigorously. In tandem, a solution containing 372 µL $AgNO_3$ (0.1 M) and 280 µL $MgSO_4$ (0.1 M) was stirred vigorously for 5 minutes. When the water was boiling, 341 µL of fresh trisodium citrate (0.1 M) and 25 µL of ascorbic acid (0.1 M) were added to the reaction mixture and agitated for 1 minute. Then, 130.1 µL of the $AgNO_3/MgSO_4$ solution was added, and the reaction turned pale yellow then orange. The system was covered with tin foil and agitated for an additional 5 minutes. After this time, the system was cooled to RT then stored in the refrigerator.

VI. Inverse Method Protocol for SERS

An aliquot of synovial fluid was warmed to RT from −80° C., and 2.5 µL were deposited on a clean microscope slide. The drop deposit was covered and dried overnight. Then, 3.5 µL of silver colloids were deposited on top of the SF drop and left to dry for at least 2 hours before the SERS analysis was performed. The silver colloid solution added on the SF samples was obtained by centrifuging 500 µL of the initial solution of silver nanoparticles 4 times, followed by dispersion in 20 µL of water.

CONCLUSION

According to the method of the invention, the vibrational signatures of arthritic synovial fluids via surface-enhanced Raman spectroscopy are obtained.

According to the invention, colloidal AgNPs were seen to be more effective than AuNPs in enhancing the biofluid signature. Nonetheless, after working in numerous conditions and after testing other published SERS substrates, a potential biosignature for unadulterated arthritic synovial fluid was, to the best of our knowledge, achieved for first time. This biosignature was acquired using a protocol where the silver nanoparticles were deposited on top of dried biofluid samples, which we called the inverse method. The reproducibility of this method was tested on 43 different synovial fluid samples, and the similar signatures indicated that it was a reliable means to obtain the SERS biosignatures (FIG. 6).

Thus, the method of the present invention allows to indicate that each joint disease has an inherently unique biosignature with the peak intensity differences information. Advantageously, a library of joint disease biosignatures could be used by analyzing several samples with different pathologies. This kind of library is of interest to improve the efficiency of the diagnosis and could be optionally used as a tool for diagnosing these pathologies.

The invention claimed is:

1. A SERS method for analyzing a biological sample which is a viscous biofluid, the method comprising the step of:
   a. depositing at least one droplet of the biological sample onto a microscope slide, and drying the droplet,
   b. depositing a drop of an aqueous dispersion of metallic nanoparticles above the droplet dried in step a), to have a dense distribution of nanoparticles on a surface of the dried droplet and to obtain a SERS-activated biological sample,
   c. drying the SERS-activated biological sample,
   d. irradiating the SERS-activated biological sample using a light source to obtain a SERS spectrum, and
   e. collecting the SERS spectrum.

2. The method according to claim 1, wherein the biological sample which is a viscous biofluid has a viscosity between 0.6 to 14 poise.

3. The method according to claim 1, wherein the dense distribution of nanoparticles is $3 \times 10^{16}$ nanoparticles/$m^2$.

4. The method according to claim 1, wherein the biological sample which is a viscous biofluid is a synovial fluid previously obtained from a patient.

5. The method according to claim 1, wherein the metallic nanoparticles are colloidal metallic nanoparticles.

6. The method according to claim 5, wherein the colloidal metallic nanoparticles comprise silver.

7. The method according to claim 1, wherein in the step a) of drying the droplet of the biological sample is realized at least two hours before depositing the nanoparticles onto the top of the dried biological sample.

8. An in vitro method for diagnosing or identifying, from a biological sample which is a viscous biofluid, a joint disease, wherein the method comprises the steps of:
   a. depositing at least one droplet of said biological sample onto a microscope slide, and drying the droplet,
   b. depositing a drop of an aqueous dispersion of metallic nanoparticles above the droplet dried in step a), to have a dense distribution of nanoparticles on a surface of the dried droplet and to obtain a SERS-activated biological sample,
   c. drying the SERS-activated biological sample,
   d. irradiating the SERS-activated biological sample using a light source to obtain a SERS spectrum, and
   e. collecting and analyzing the SERS spectrum.

9. The method according to claim 8, wherein analyzing the SERS spectrum comprises the following sequential steps:
   i. a pre-processing step for correcting spectral interferences of said SERS spectrum to normalize them,
   ii. a step of selecting features and/or reducing data to identify discriminant wavenumbers, and
   iii. a step of construction of a supervised classification model using machine learning for automatic prediction of new samples.

10. A method utilizing a kit having a SERS substrate, a Raman device, and a computing device configured to determine or identify a joint disease in a biological sample based on a spectral content information, the method including analyzing a biological sample, which is a viscous biofluid, the analyzing, comprising the steps of:
   a. depositing at least one droplet of the biological sample onto a microscope slide, and drying the droplet,
   b. depositing a drop of an aqueous dispersion of metallic nanoparticles above the droplet dried in step a), to have a dense distribution of nanoparticles on a surface of the dried droplet and to obtain a SERS-activated biological sample, c. drying the SERS-activated biological sample, d. irradiating the SERS-activated biological sample using a light source to obtain a SERS spectrum, and e. collecting the SERS spectrum.

11. The method of claim 10, wherein the computing device is further configured to execute the following sequential steps:

i. a pre-processing step for correcting spectral interferences of a SERS spectrum and normalize them, ii. a step of selecting features and/or reducing data to identify discriminant wavenumbers, and iii. a step of construction of a supervised classification model using machine learning approaches for automatic prediction of new samples.

12. The method of claim 10, further comprising a step of using the kit to diagnose or identify a joint disease in a subject.

* * * * *